United States Patent [19]

Gallo

[11] Patent Number: 4,472,504
[45] Date of Patent: Sep. 18, 1984

[54] HYPERPRODUCING CELLULASE MICROORGANISM

[75] Inventor: Benedict J. Gallo, Natick, Mass.

[73] Assignees: The United States of America as represented by the Secretary of the Army, Washington, D.C.; The United States of America as represented by the Secretary of the Army, Washington, D.C.

[21] Appl. No.: 479,221

[22] Filed: Mar. 28, 1983

[51] Int. Cl.³ .................... C12N 9/42; C12N 1/22; C12N 1/14; C12N 1/885
[52] U.S. Cl. .................................. 435/209; 435/252; 435/254; 435/945
[58] Field of Search ............... 435/209, 254, 945, 252

[56] References Cited

U.S. PATENT DOCUMENTS 4,275,163  6/1981  Gallo .................................. 435/209

FOREIGN PATENT DOCUMENTS 591502  2/1978  U.S.S.R. ............................. 435/209

Primary Examiner—Lionel M. Shapiro
Attorney, Agent, or Firm—Anthony T. Lane; Robert P. Gibson; Lawrence E. Labadini

[57] ABSTRACT

A process and a microorganism for synthesizing cellulase enzymes and soluble proteins are described. The microorganism is a mutant strain of an Ascomycete fungus capable of the synthesizing cellulases and soluble proteins in the presence of a growth medium containing cellulose, cellulose enzymic hydrolysate sugars or lactose. The mutant strain is identified as *T. reesei* MCG80.

11 Claims, No Drawings

HYPERPRODUCING CELLULASE MICROORGANISM

The invention described herein may be manufactured, used, and licensed by or for the Government for governmental purposes without the payment to me of any royalty thereon.

BACKGROUND AND PRIOR ART

Cellulose constitutes the major storage form of photosynthesized glucose, and the major component of solar energy converted to biomass. World wide demand for energy and for food supplies are increasing. Cellulose is an attractive raw material for supplying these needs, because of its abundance. The glucose subunits of cellulose can be used in a variety of processes for production of energy on the one hand or for the production of protein on the other. A major difficulty which has stood athwart the advance of cellulose utilization technology has been the difficulty of obtaining glucose in reasonable yield from cellulose at a reasonable cost in terms of energy input, equipment requirements and the like. Enzyme-catalyzed hydrolysis of cellulose is an attractive potential solution to these difficulties. However, the production of adequate amounts of cellulase is dependent upon obtaining a suitable source of large quantities of the enzyme in a reasonably pure state.

Cellulases are found in the digestive tracts of snails, in certain anaerobic bacteria and in other microorganisms, for example the rumen microorganisms which inhabit digestive tracts of ruminants. A number of fungal species are known to produce cellulase, including fungi of the class Ascomycetes, such as Neurospora and Trichoderma. The fungal systems are perhaps the most attractive because the organisms can be cultured without resort to unusual growth conditions and some, at least, are capable of rapid growth.

The fungal system described herein is derived from *Trichoderma reesei*, herein *T. reesei*, an Ascomycete fungus species formerly assigned to the species *Trichoderma viride*. In general, any Ascomycete fungus capable of synthesizing a complete cellulase could be used to derive a strain having similar properties. *T. reesei* is presently preferred because large amounts of cellulase are produced extracellularly. See, Simmons, E. G., *Abstracts of Second International Mycology Congress*, Tampa, Fla., page 618 (1977). The cellulolytic system of enzymes by this species include an endo-$\beta$ glucanase, exo-$\beta$-glucanase, and $\beta$-glucosidase. The first of these enzymes is capable of hydrolyzing $\beta$-glucosidic bonds at mainly internal sites on the cellulose molecule. The second is capable of catalyzing the hydrolytic removal of disaccharide subunits from the ends of the cellulose chain, yielding mainly cellobiose as a product. The $\beta$-glucosidase catalyzes the hydrolysis of cellobiose to glucose. The term cellulase, as used herein, includes all such enzymes and their isozymes. The cellulase produced by *T. reesei* is found as soluble protein in the growth medium. Synthesis of cellulase by wild type *T. reesei* is under stringent metabolic and genetic control, in which both induction and repression are observed. The term induction is used herein to mean the presence of a substance necessary for the synthesis of the enzyme by the organism. Repression is a term used to describe the phenomenon in which the presence of a substrate in the growth medium is sufficient to prevent the synthesis of the enzyme. The presence of a repressor substance for a particular enzyme prevents the expression of the gene coding for that enzyme, and in some cases the presence of an inducer substance is additionally required for expression of the gene. In cultures of wild type *T. reesei*, cellulose acts as an inducer of the cellulolytic complex exclusive of $\beta$-glucosidase and its presence is therefore required in the medium to obtain appreciable levels of these enzymes. A number of substrates act as repressors, notably glucose and glycerol. The necessary conditions for cellulase synthesis therefore are the presence of cellulose or other inducing substrates such as lactose and the near absence of glucose. However, as cellulase is synthesized and cellulose in the medium is degraded, glucose is produced, which may result in the repression of enzyme synthesis. Consequently, the levels of cellulase produced by the wild type strain are never very great. Furthermore, the synthesis of cellulase is characterized by a lag period due to the presence of a repressor substance. Once the growth medium has been exhausted of the repressor substance, synthesis of cellulase even in the presence of an inducer, does not begin for several hours. Consequently, maximal enzyme production requires mutational alteration of the wild type strain so as to lessen the stringent metabolic and genetic controls normally limiting the production of cellulase.

SUMMARY OF THE INVENTION

The present invention concerns a mutant strain of a microorganism which is unique in its ability to produce substantial quantities of extracellular soluble protein in the form of cellulase enzymes. The microorganism is a strain of *T. reesei*, designated as MCG80, which is derived from *T. reesei* strain RUT-C30.

*T. reesei* MCG80 has the following significant properties: The organism produces cellulase and accessory enzymes as extracellular soluble protein at a rate and in an amount greater than that obtained with hyperproducing strain MCG77 or RUT-C30. In addition to cellulose, the synthesis of cellulase/soluble proteins by this strain is inducible by cellulose enzymic hydrolysate sugars and lactose. The organism is genetically haploid when grown in laboratory culture conditions and is, therefore, exactly reproducible from one generation to the next without genetic variation.

*T. reesei* MCG80 was placed on deposit in the Agricultural Research Culture Collection (NRRL), Northern Regional Research Center, U.S. Department of Agriculture, 1815 N. University St., Peoria, Ill. 61604, U.S.A. The strain is designated NRRL12368.

DETAILED DESCRIPTION OF THE INVENTION

Strain MCG80 was derived from *T. reesei* strain RUT-C30 (developed at Rutgers University) as described by Montenecourt, B. S., et al., *Biotech, Bioeng Symp. No.* 10, pgs 15–26 (1980) through a series of steps consisting of ultraviolet light mutagenesis, spore transferrance to Kabicidin agar plates and incubation for growth. The colonies which survived this fungicide treatment were isolated and tested for cellulase production in liquid culture. One strain, designated MCG80 was found to be superior to other known hyperproducing strains of the *T. reesei* in its ability to synthesize cellulase and soluble protein.

The strain of this invention is maintained on agar slants containing Vogel salts supplemented with biotin, 0.00005% (w/v) and cellulose, 1.25%–2.25% (w/v).

See Difco Manual 9th Edition (1953), Difco Laboratories, Inc., Detroit, Mich. and also the description in Vogel, H. *Amer. Nat.* 98, page 435 (1964).

Inoculum cultures were started with conidia from the agar slants which were grown for 3 days in the basic salt medium described by Mandels, M., *Symposium on Cellulose as a Chemical and Energy Source,* Biotech-Bioeng. Symp. No. 5, Wiley Interscience, New York, page 861 (1975) except that urea was omitted and 0.1% (w/v) proteose peptone and 0.1% (w/v) Tween 80 Trademark, ICI United States, Wilmington, Del., were added. Temperature was maintained 27°-28° C.

Fermentation was carried out using Magnaferm Fermentors Model MA114, New Brunswick Science Co., New Brunswick, N.J., in a submerged culture having a working volume of 10 liters. The sterile growth medium was the basic salt medium described by Mandels, M. (supra) except that the medium salts were at double concentration and urea was omitted. The substrate used was BW200 ball milled cellulose pulp (Brown Co., Gerlin, N.H.) or Avicel PH105 microcrystalline cellulose (FMC Corp., American Viscose Division, Newark, Del.) or 2% lactose and contained 0.1% Tween 80. In some examples, biotin and/or proteose peptone were added to the medium. The culture was incubated at a rate to maintain positive dissolved oxygen and good mixing by delivering 2-6 liters per minute flow at 5-10 psig pressure. The medium was agitated by a propeller at 300-900 rpm. Each fermentation was started with a 10% (v/v) inoculum. An antifoam agent is used as needed.

Enzyme activity is expressed in International Units per ml. One unit of activity is the amount of enzyme catalyzing release of one micromole of glucose per minute. Cellulase was measured using a standing filer paper (FP) assay as described in Gallo, B. J., et al, *"Cellulase Process Improvement and its Economics"* in *Advances in Biotechnology: Fermentation and Yeasts,* Vol. 3 (1981) pp 281-288 or by carboxymethylcellulose (CMC) as described in Andreotti, R. D., et al., *Proceedings of the Bioconversion Symposium,* New Delhi, India, page 249 (1977). $\beta$-glucosidase is measured in international units using salicin, as described by Mandels, M., et al., *Biotech. Bioeng. Symp. No.* 6, Wiley Interscience, New York, Page 21 (1976). Filter paper and cotton are used as substrates to measure the activity of the total cellulase system. Carboxymethylcellulose is used as a substrate to measure the activity of the endo-$\beta$-glucanase. Cellulase productivity is expressed as Filter Paper Units (FPU) of cellulase produced per liter of culture filtrate per hour.

Reducing sugar is measured as glucose by a dinitrosalicylic acid procedure described in Miller, G. L., *Anal. Chem* 31, page 426 (1959). The dry weight of whole culture solids is determined by the procedure described in Gallo, B. J. et al., *Biotech. Bioeng. Symp. No.* 8, page 89 (1978). Measurement of cellulase and soluble protein content was made on a glass fiber filtered culture filtrate was obtained by using the protein assay of Lowry, O. H. et al., *J. Bio. Chem.* 193, page 265 (1951).

In terms of its morphology, strain MCG80 is classified as a semiparamorphic mutant which shows restricted distal growth on potato dextrose agar(PDA) plates and, in this manner, is similar to *T. reesei* strain MCG77. It does not spread rapidly over medium surfaces as do other nonparamorphic strains of *T. reesei*. On PDA medium, strain MCG80 does, however, conidiate poorly and forms a compact mycelial colony. Strain MCG80 is best distinguished from other mutant strains MCG77 and RUT-C30, in the amount of extracellular cellulase/soluble protein it can produce when grown on cellulase inducing substrates and by the rate at which cellulase/soluble protein is produced.

In addition to cellulose and cellulose hydrolyzate sugars, MCG80 also is inducible by lactose. The ability to recognize inducer analogs such as lactose offers a number of distinctive methodological advantages. The ability to work with soluble materials in the fermentation reduces engineering problems associated with insoluble substances in a fermentation. There will be no loss of cellulase due to adsorption on the surface of residual cellulose. Fermenter volume is used more efficiently, since a greater proportion can be devoted to fungal biomass and less energy is required to agitate and aerate the fermenter. In addition, the amount of inducer can be increased since there is no limitation imposed by bulk as there is with cellulose. More significantly, lactose is a major constituent of whey, which is a waste by-product of the cheese making industry. A large supply of an inexpensive by-product is therefore available for low cost production of cellulase. Use of a soluble substrate easily allows the use of a continuous culture enzyme production and its control for maximum production.

Example 1

A 10 liter batch of growth medium containing 8% (w/v) BW200 cellulose pulp, double concentraction of salts as described above, 0.1% Tween 80, and 0.1% preteose peptone was placed in a Magnaferm fermentor and autoclaved. Biotin was dissolved in 50% ethanol solution and autoclaved. After cooling, 200 ug of the biotin was added to the seed inoculum culture immediately prior to fermentation inoculation. The fermentation was started with a 10% (v/v) inoculum culture of MCG80. The batch was incubated at 28°±0.5° C. and the pH was set initially at pH 5.0 and allowed to fall to 3.75 and controlled at that level for the first 48 hours and than at 3.5 for the remaining time. The pH of the batch was controlled with 2N NH$_4$OH. The cellulase titer of the culture filtrate expressed in FPU per ml is 17.2. Cellulase activity is reported as (1) Highest Titler (HT) which represents the cellulase produced from start of the fermentation to the time when maximum cellulase Titler is first reached and (2) Maximum cellulase productivity which represents the slope of the linear part of the cellulase production curve. The HT is 142 FPU/1/hr and the Maximum productivity at 240 FPU/1/hr.

Example 2

A ten liter batch of growth medium containing 9% Avicel PH105 microcrystalline cellulose, double concentration of salts, 0.1% Tween 80, and 0.3% proteose peptone, was placed in the fermentor. The fermentation was started with a 10% (v/v) seed inoculum of MCG80 grown on 1% Avicil PH105 microcrystalline cellulose medium containing regular salts with 0.2% Tween 80 and 0.1% proteose peptone and inoculated for 3 days at 20° C. on a reciprocal shaker. Before inoculation, 400 $\mu$g of biotin prepared as in Example 1 was added to the seed inoculum culture. The batch was incubated at 28±0.5° C. and the pH was set as in Example 1 and was maintained at 3.75 for 48 hours and at 3.5 for the remainder of the fermentation. The cellulase titer of the culture filtrate is 23.4 FPU/ml. The soluble protein yield after 10 days of fermentation was 35.5 mg per ml of filtrate. A HT cellulase productivity of 102 FPU/1/hr and a Maximum cellulase productivity of 157 FPU/1/hr were attained. High carboxymethylcellulase (endo $\beta$-glucanase) and $\beta$-glucosidase activities were also produced. 470 carboxymethylcellulase unit per ml and 1.7 $\beta$-glucosidase units per ml were produced after 10 days.

Example 3

Lactose as an inducer of cellulase and soluble protein formation was determined with respect to MCG80, MCG77 and RUT-C30 strain of *T. reesei*. Ten liter batches of growth medium each containing 2% (w/v) lactose, double concentration of salts and 0.1% Tween 80 were each inoculated with one of the strains. The pH of growth medium was set as in Example 1 and was controlled at 3.5. Each strain was culture incubated in a separate flask containing 1% lactose, standard salts, 0.2% Tween 80 and 0.1% proteose peptone at 29° C. for 3 days on a gyratory shaker. 10% (v/v) seed inculum from each cultured strain was transmitted to a separate fermentor containing growth medium. Strain MCG80 attained 1.7 FPU per ml after 45 hours and a HT cellulase productivity of 40.5 FPU per liter per hour and a Maximum cellulase productivity of 90 FPU per liter per hour. Strain MCG70 achieved the same cellulase titer as MCG80 after 70 hours but had lower HT and Maximum cellulase activities of 24 FPU per liter per hour and 36 FPU per liter per hour, respectively. Strain RUT-C30 produced 0.7 FPU per ml of culture filtrate after 60 hours and attained an HT and Maximum cellulase productivity of 12 FPU per liter per hour and 21 FPU per liter per hour, respectively. The high cellulase titer and high cellulase productivity that are obtained by strain MCG80 when grown on lactose in the absence of proteose peptone are major differences which distinguish that strain from MCG77 and RUT-C30.

Growth of the novel strain of this invention, MCG80, on a cellulose, cellulose enzymic hydrolysate sugar or lactose substrate produces significant quantities of soluble protein which can be readily harvested and used for agriculture purposes as a feed supplement for live stock and industrially as a protein source for manufacturing proteose peptone or other products. The soluble proteins collectively contain all of the essential amino acids.

The cellulase enzymes produced by this strain are also used for the enzyme-catalyzed hydrolysis of cellulose materials.

What is claimed is:

1. A biologically pure culture of *T. reesei* strain MCG80.

2. A biologically pure culture according to claim 1 wherein said culture has the capability to synthesize cellulase enzymes.

3. A biologically pure culture according to claim 2 wherein the synthesis of the cellulase enzymes by the organism is induced by cellulose, cellulose enzymic hydrolysate sugars or lactose.

4. A process for producing enzymes capable of catalyzing the hydrolysis of cellulose comprising:
   (a) inoculating a suitable sterile growth medium with *T. reesei* strain MCG80, said growth medium containing an inducer of cellulase synthesis, and
   (b) incubating the inoculated growth medium under conditions which will permit the growth of MCG80.

5. A process according to claim 4 wherein the inducer of cellulase synthesis is cellulose.

6. A process according to claim 5 wherein the pH is maintained at 3.75 for the first 48 hours of incubation and then at 3.5 for the remainder of the incubation.

7. A process according to claim 4 wherein the inducer of cellulase synthesis is lactose.

8. A process according to claim 7 wherein the pH is maintained at 3.5 during the incubation.

9. A process for producing soluble protein from cellulose, cellulose enzymic hydrolysate sugar or lactose substrate which comprises:
   (a) inoculating sterile growth medium containing a substrate selected from the group consisting of cellulose, cellulose enzymic hydrolysate sugar and lactose with *T. reesei* strain MCG80, and
   (b) incubating the inoculated growth under conditions which will permit the growth of strain MCG80.

10. A process according to claim 9 wherein the substrate is cellulose and wherein the pH is maintained at 3.75 for the first 48 hours of incubation and at 3.5 for the remainder of the incubation.

11. A process according to claim 9 wherein the substrate is lactose and wherein the pH is maintained at 3.5 during incubation.

* * * * *